US011549227B1

(12) United States Patent
Wang et al.

(10) Patent No.: US 11,549,227 B1
(45) Date of Patent: Jan. 10, 2023

(54) EXPERIMENTAL SETUP FOR MEASURING THE VACUUM DEGREE AND PORE PRESSURE AT A POINT OF SOIL MASS IN VACUUM CONSOLIDATED STATE AND THE TEST OPERATION METHOD THEREOF

(71) Applicants: Peng Wang, Wenzhou (CN); Xueyan Ge, Wenzhou (CN); Quanyang Dong, Wenzhou (CN); Yang Zhou, Wenzhou (CN); Xiaotian Yang, Wenzhou (CN)

(72) Inventors: Peng Wang, Wenzhou (CN); Xueyan Ge, Wenzhou (CN); Quanyang Dong, Wenzhou (CN); Yang Zhou, Wenzhou (CN); Xiaotian Yang, Wenzhou (CN)

(73) Assignee: Wenzhou University, Wenzhou (CN)

( * ) Notice: Subject to any disclaimer, the term of this patent is extended or adjusted under 35 U.S.C. 154(b) by 0 days.

(21) Appl. No.: 17/348,787

(22) Filed: Jun. 16, 2021

(51) Int. Cl.
*E02D 1/02* (2006.01)
*G01N 33/24* (2006.01)

(52) U.S. Cl.
CPC ............. *E02D 1/027* (2013.01); *G01N 33/24* (2013.01)

(58) Field of Classification Search
CPC ............................... E02D 1/027; G01N 33/24
See application file for complete search history.

(56) References Cited

FOREIGN PATENT DOCUMENTS

| CN | 200996923 Y | * | 12/2007 |
| CN | 101149323 A | * | 3/2008 |
| CN | 102564900 A | * | 7/2012 |
| CN | 112683935 A | * | 4/2021 |
| CN | 112781995 A | * | 5/2021 |

* cited by examiner

Primary Examiner — Ryan D Walsh

(57) ABSTRACT

An experimental setup for measuring the vacuum degree and pore pressure at a point of soil mass in vacuum consolidated state, including a connecting tube, the connecting tube includes an upper water storage tube, a middle tube, the middle tube is loaded with an upper experimental soil mass, the lower tube is loaded with a lower experimental soil mass, a water storage chamber is connected to a pumping mechanism, an intermediate inner chamber is connected to a negative pressure vacuum gauge, the inlet conduit is connected to a negative pressure vacuum gauge. Additionally, the present invention provides a test operation method. The device measures the vacuum degree of upper part of experimental soil mass by observing the reading in the negative pressure vacuum gauge.

9 Claims, 6 Drawing Sheets

EXPERIMENTAL SETUP FOR MEASURING THE VACUUM DEGREE AND PORE PRESSURE AT A POINT OF SOIL MASS IN VACUUM CONSOLIDATED STATE AND THE TEST OPERATION METHOD THEREOF

BACKGROUND OF INVENTION

1. Field of the Invention

The present invention relates generally to an experimental setup for measuring the vacuum degree and pore pressure at a point of soil mass in vacuum consolidated state, and more particularly to the research on the attenuation in vacuum consolidated state, so as to provide scientific and effective information. Additionally, it relates to the test operation method of the experimental setup.

2. Description of Related Art

The vacuum preloading is a high vacuum densification method of drainage consolidation method, it is a new technology of rapidly reinforcing foundations, it is used for treating the foundations in soft soil regions in recent years. The vacuum preloading method is applicable to reinforcing ultra-soft foundations of construction works, especially to the earth filling of bad foundation construction, as well as to saturated homogeneous cohesive clay and cohesive clay with lice interlayer, its operating principle is to let the pore water in soil mass flow into the sand drain and drain out to implement consolidation.

However, as the consolidation proceeds, different silt thicknesses result in different degrees of consolidation, the attenuation occurs in different directions. The vacuum degree and pore water pressure of soil mass in vacuum consolidated state shall be measured. At present, the measuring instruments include vacuum gauge and pore water pressure gauge, but in the vacuumized state, the vacuum gauge is inserted into the silt, partial conduit is blocked, and it is not hollow state, the vacuum gauge fails to accurately measure the vacuum degree at a point of soil mass in vacuum consolidated state. In addition, the silt may not be in saturated state in actual construction, the accuracy of the data measured by pore pressure gauge cannot be guaranteed, and in the state of negative pressure, the contrast between the parameters of pore pressure gauge and the data of vacuum degree is poor, the mode of attenuation and the decrement are unknown.

SUMMARY OF THE INVENTION

The technical problem to be solved by the present invention is to provide an experimental setup for measuring the vacuum degree and pore pressure at a point of soil mass in vacuum consolidated state and the test operation method thereof, the experimental device can measure the vacuum degree and pore pressure data of a certain point of the underground soil more conveniently, quickly and accurately.

An experimental setup for measuring the vacuum degree and pore pressure at a point of soil mass in vacuum consolidated state, including a connecting tube, the connecting tube including an upper water storage tube, a middle tube, an intermediate inner chamber and a lower tube abutting each other, wherein the middle tube is loaded with an upper experimental soil mass, the lower tube is loaded with a lower experimental soil mass, a filter membrane is arranged at the upper and lower ends of the soil masses in the middle tube and lower tube respectively, the filter membrane is pervious, the upper water storage tube stores distilled water, the lower tube is connected to a water storage chamber through an inlet conduit, the water storage chamber is connected to a pumping mechanism through an outlet conduit, the parts other than inlet conduit and outlet conduit of water storage chamber are sealed, the intermediate inner chamber is connected to a negative pressure vacuum gauge, the inlet conduit is connected to a negative pressure vacuum gauge.

More particularly, wherein the upper water storage tube and lower tube are provided with a docking mechanism, the middle tube and lower tube are connected and driven in the soil mass to take the subsurface soil mass.

More particularly, wherein the intermediate inner chamber is arranged in the intermediate tube, the upper end of intermediate tube is connected to the middle tube, and the lower end is connected to the lower tube.

More particularly, wherein the connecting tube is provided with a mounting base, the mounting base is provided with a negative pressure vacuum gauge, a water storage chamber and a pumping mechanism, the negative pressure vacuum gauge includes an upper negative pressure vacuum gauge and a lower negative pressure vacuum gauge, the mounting base includes a base, a spindle and a mounting rack, the sleeving hole of mounting rack is fitted over the spindle, moving up and down along the spindle, an unlockable lock bar is arranged at the sleeve joint of mounting rack and spindle, the lock bar is provided with a handwheel, the lock bar is rotationally connected to a locking tile in the sleeving hole through the mounting rack, the intermediate tube is fixed to the mounting rack, the upper negative pressure vacuum gauge is fixed to the mounting rack, the intermediate tube communicates with the upper negative pressure vacuum gauge through the upper channel on the mounting rack; the base is provided with an abutting port for abutting the lower tube, the abutting port is connected to the lower channel on the base, the water storage chamber, lower negative pressure vacuum gauge and pumping mechanism are fixed to the base, the lower negative pressure vacuum gauge communicates with the lower channel, the outer end of the lower channel is connected to the water storage chamber, the water storage chamber is connected to the pumping mechanism.

More particularly, wherein a storage camera aligned with the negative pressure vacuum gauge dial is arranged outside the negative pressure vacuum gauge.

More particularly, wherein an electronic readout system is arranged outside the negative pressure vacuum gauge, the electronic readout system is connected to the computer, the computer records the data of negative pressure vacuum gauge at any time.

More particularly, wherein an electronic readout system is arranged outside the negative pressure vacuum gauge, the electronic readout system is connected to the computer, the computer records the data of negative pressure vacuum gauge at any time.

More particularly, wherein the upper test soil mass is in a hard tube, the upper end and lower end of the upper test soil mass are covered with a filter membrane respectively, the upper test soil mass is sealed with distilled water, the distilled water tube is covered with a thin film to guarantee a vacuum environment.

More particularly, wherein the upper filter membrane of the upper test soil mass is connected to a pore pressure gauge, the pore pressure gauge is connected to the computer for reading.

A test operation method of the experimental setup for measuring the vacuum degree and pore pressure at a point of soil mass in vacuum consolidated state defined in Claim 4, including the following steps:

1. the middle tube and lower tube are connected in one, and then the middle tube and lower tube are installed on a boring machine, the soil sampling depth is approached by mud drilling, when the soil sampling depth is approached, the descent shall be slow to avoid disturbing the hole bottom soil sample, the middle tube and lower tube are rapidly and continuously pressed in the predetermined depth of soil, and stopped for 3-5 minutes before the soil mass is pulled out;

2. when the middle tube is being separated from the lower tube, the soil mass therein is cut up into an upper test soil mass remaining in the middle tube and a lower experimental soil mass remaining in the lower tube, the filter membrane is disposed at the upper and lower ends of the middle tube respectively, the filter membrane is disposed at the upper and lower ends of the lower tube respectively, the lower end of the middle tube is connected to the upper end of the intermediate tube, the upper end of the lower tube is connected to the lower end of intermediate tube, the lower end of lower tube abuts the abutting port, the upper water storage tube is filled with equilong distilled water;

3. after various devices are connected up, the pumping mechanism is actuated, various instruments have readings after a period of time, if the reading of negative pressure vacuum gauge is $k_1$, the reading of negative pressure vacuum gauge is $k_2$, the reading of pore pressure gauge is $k_3$, and the heights of upper experimental soil mass and lower experimental soil mass are fixed at l, the attenuation law and specific attenuation value are analyzed by comparing the values of $$\frac{k_1 - k_2}{l}$$

and $$\frac{k_2 - k_3}{l}.$$

Technical Effects of the Present Invention

1. The device measures the vacuum degree of upper part of experimental soil mass by observing the reading in the negative pressure vacuum gauge, the test data can be obtained more accurately, and the overall operating procedure uses multisection tube connection, and the data are recorded in time by camera or electronic readout system and computer, so the data can be obtained more accurately, and the installation and dismounting are more convenient, it is workable to form more sections of subsurface soil mass to obtain more diversified vacuum degree data.

2. Due to the tube structure, the middle tube and lower tube to be inserted into the soil mass can be directly driven into the soil mass to obtain experimental soil from relevant position, the obtained test soil mass is closer to the real environment, and it is more convenient to be obtained, it is available for test once the mounting base is installed, the test efficiency can be increased greatly, and the test difficulty is reduced.

3. The device uses monolithic construction, the main components are integrated on the base, spindle and mounting rack which form the mounting base, which are portable and convenient for rapidly building a testing system, favorable for site operation.

DETAILED DESCRIPTION OF THE INVENTION

The present invention is further described below with attached figures and embodiments. Please note that the words "front", "back" "left", "right", "upper" and "lower" used in the following description refer to directions in the attached figures. The words "bottom surface" and "top surface", "inner" and "outer" refer to the directions toward or away from the geometric center of specific component.

Figure 1:
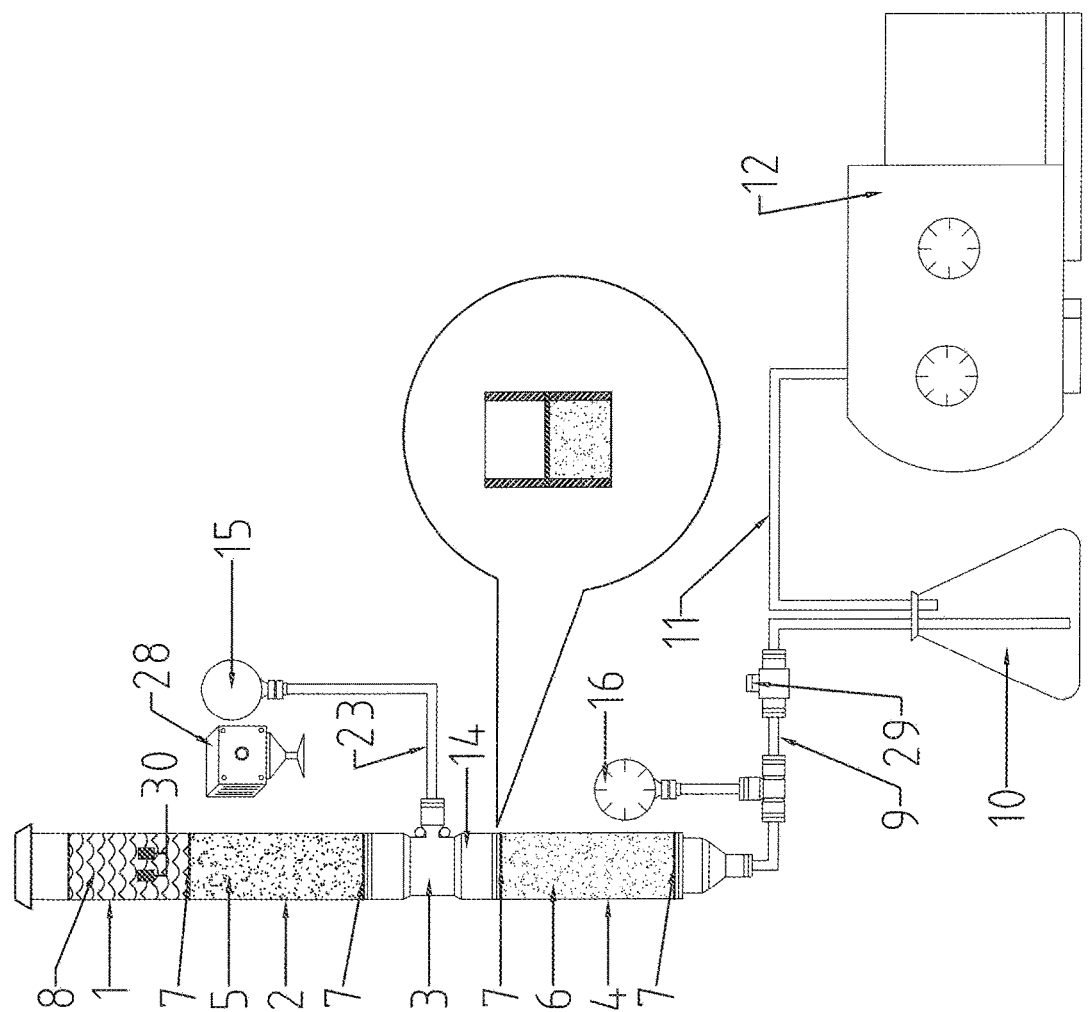
FIG. 1 is a structural representation of experimental setup for measuring the vacuum degree and pore pressure at a point of soil mass in vacuum consolidated state provided in the Embodiment 1 of the present invention.
Figure 2:
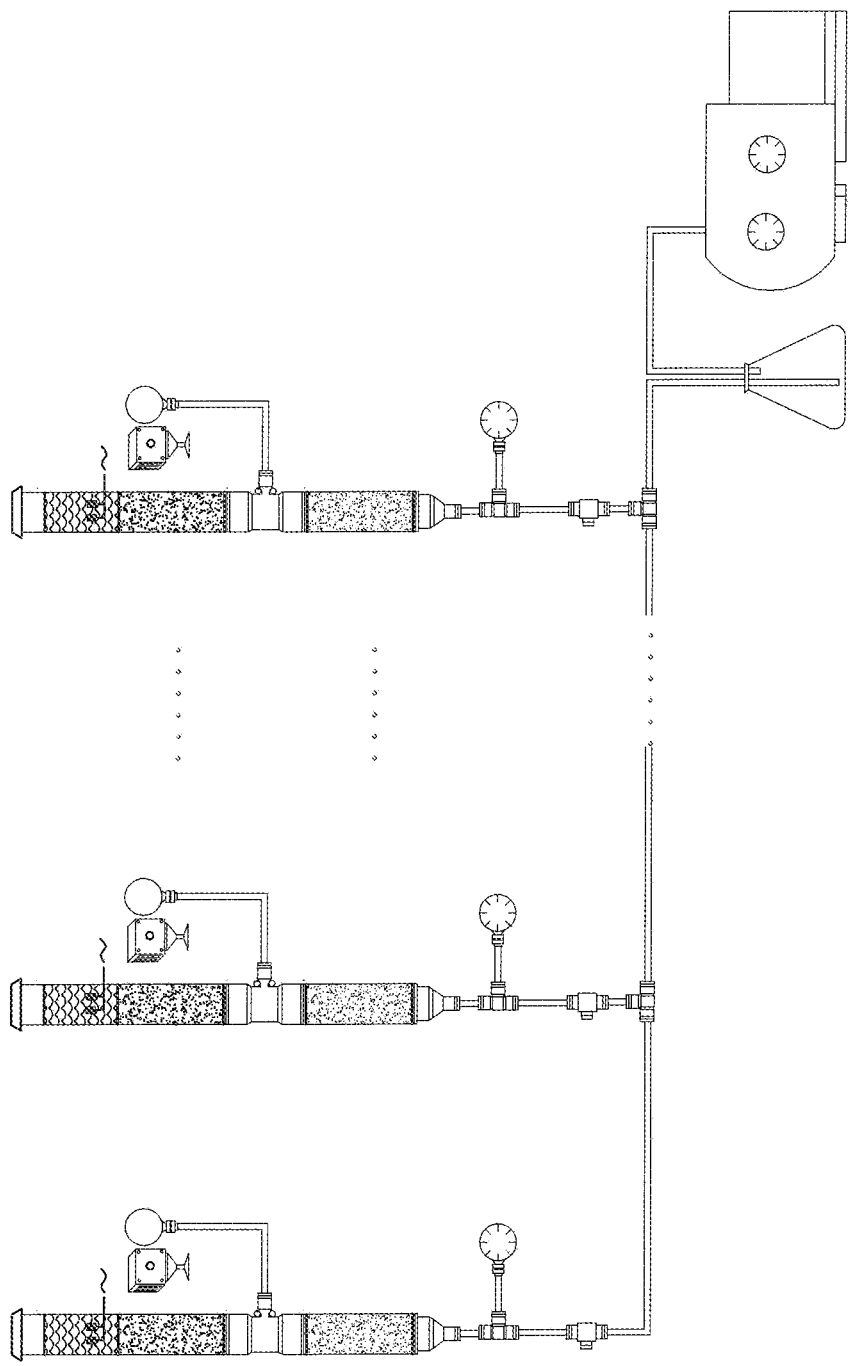
FIG. 2 is a structural representation of experimental setup for measuring the vacuum degree and pore pressure at a point of soil mass in manifold vacuum consolidated state.

As shown in FIGS. 1-2, the experimental setup for measuring the vacuum degree and pore pressure at a point of soil mass in vacuum consolidated state provided in the Embodiment 1 of the present invention includes a connecting tube, the connecting tube includes an upper water storage tube 1, a middle tube 2, an intermediate inner chamber 3 and a lower tube 4 abutting each other, the middle tube 2 is loaded with an upper experimental soil mass 5, the lower tube 4 is loaded with a lower experimental soil mass 6, a filter membrane 7 is arranged at the upper and lower ends of the soil masses in the middle tube 2 and lower tube 4 respectively, the filter membrane 7 is pervious, the upper water storage tube 1 stores distilled water 8, the distilled water 8 simulates the groundwater, the lower tube 4 is connected to a water storage chamber 10 through an inlet conduit 9, the water storage chamber 10 is connected to a pumping mechanism 12 through an outlet conduit 11, a turn switch 29 is arranged at the outlet conduit 11, the pumping mechanism 12 is a water pump, the parts other than inlet conduit 9 and outlet conduit 11 of water storage chamber 10 are sealed, the intermediate inner chamber 3 is connected to the negative pressure vacuum gauge, the inlet conduit 9 is connected to the negative pressure vacuum gauge. The middle tube 2 and lower tube 4 are provided with a docking mechanism, the docking mechanism generally uses threaded connection or flanged connection, the middle tube 2 and lower tube 4 are connected and driven into the soil mass to take subsurface soil mass. The intermediate inner chamber 3 is disposed in an intermediate tube 14, the upper end of intermediate tube 14 is connected to the middle tube 2, and the lower end is connected to the lower tube 4.

As shown in FIGS. 3-6, the Embodiment 2 is basically identical with the Embodiment 1 of the present invention, the only, difference is that the connecting tube is provided with a mounting base, and the mounting base is provided with a negative pressure vacuum gauge, a water storage chamber 10 and a pumping mechanism 12, the negative pressure vacuum gauge includes an upper negative pressure vacuum gauge 15 and a lower negative pressure vacuum gauge 16. The mounting base includes a base 17, a spindle 18 and a mounting rack 19, the sleeving hole of mounting rack 19 is fitted over the spindle 18, moving up and down along the spindle 18, an unlockable lock bar 20 is disposed at the sleeve joint of mounting rack 19 and spindle 18, the lock bar 20 is provided with a handwheel 21, the lock bar 20 is rotationally connected to a locking tile 22 in the sleeving hole through the mounting rack 19. The intermediate tube 14 is fixed to the mounting rack 19, the upper negative pressure vacuum gauge 15 is fixed to the mounting rack 19, the intermediate tube 14 communicates with the upper negative pressure vacuum gauge 15 through the upper channel 23 on the mounting rack 19; the base 17 is provided with an abutting port 24 for abutting the lower tube 4, the abutting port 24 is connected to the lower channel 25 on the base 17, the water storage chamber 10, lower negative pressure vacuum gauge 16 and pumping mechanism 12 are fixed to the base 17, the lower negative pressure vacuum gauge 16 communicates with the lower channel 25, the outer end of the lower channel 25 is connected to the water storage chamber 10, the water storage chamber 10 is connected to the pumping mechanism 12. An annular step face 26 is formed at the abutting port 24, the inner side face of annular step face 26 is threaded for connecting the lower tube 4, a seal ring 27 is arranged between the bottom of the annular step face 26 and lower tube 4, the upper water storage tube 1 and middle tube 2, middle tube 2 and intermediate tube 14, intermediate tube 14 and lower tube 4 use an annular step face 26 with an internal thread and a seal ring 27 respectively to form tight connection.

As shown in FIG. 1, a storage camera 28 aligned with the negative pressure vacuum gauge dial is arranged outside the negative pressure vacuum gauge, the data are collected once every ten minutes, and the data are stored. Alternatively, an electronic readout system is arranged outside the negative pressure vacuum gauge, the electronic readout system is connected to a computer, the computer records the data of negative pressure vacuum gauge at any time. The structure is favorable for long-term periodic recording, so that the test is more accurate.

Figure 3:
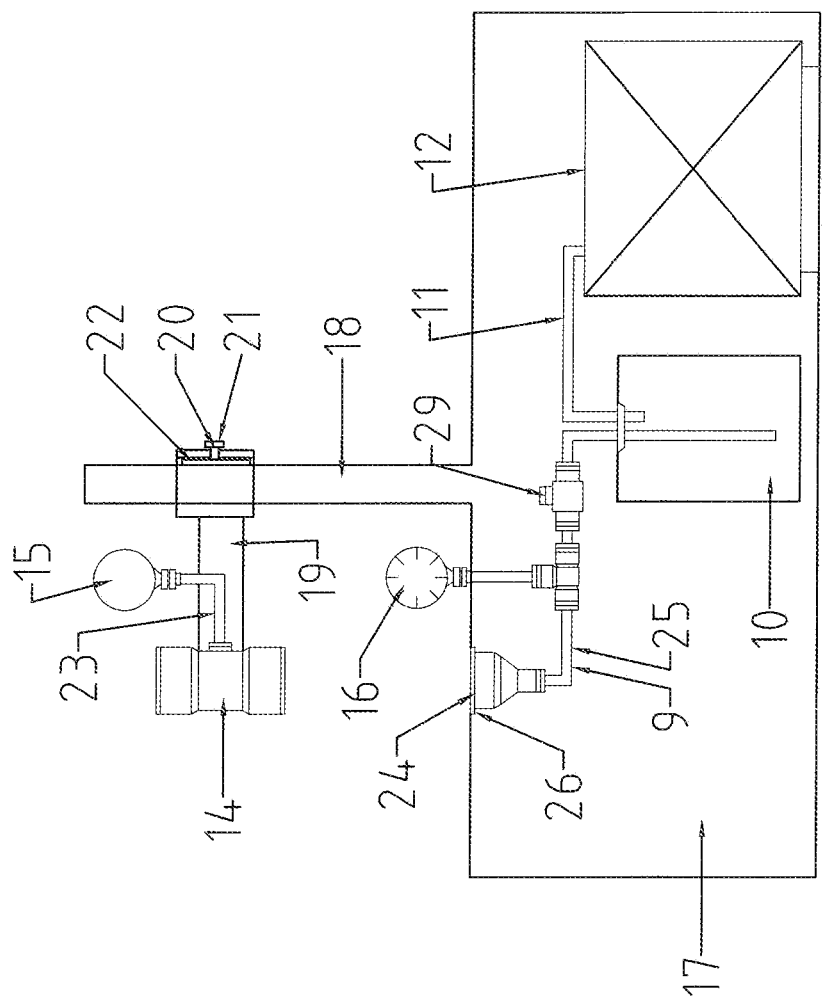
FIG. 3 is a structural representation of the experimental setup for measuring the vacuum degree and pore pressure at a point of soil mass in vacuum consolidated state provided in Embodiment 2 before the middle tube and lower tube are assembled.
Figure 4:
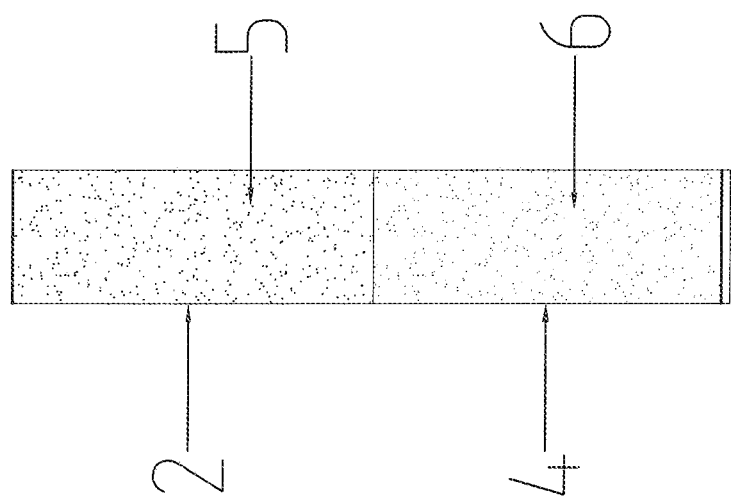
FIG. 4 is a structural representation of the middle tube and lower tube in FIG. 3 connected rim piling and soil sampling.
Figure 5:
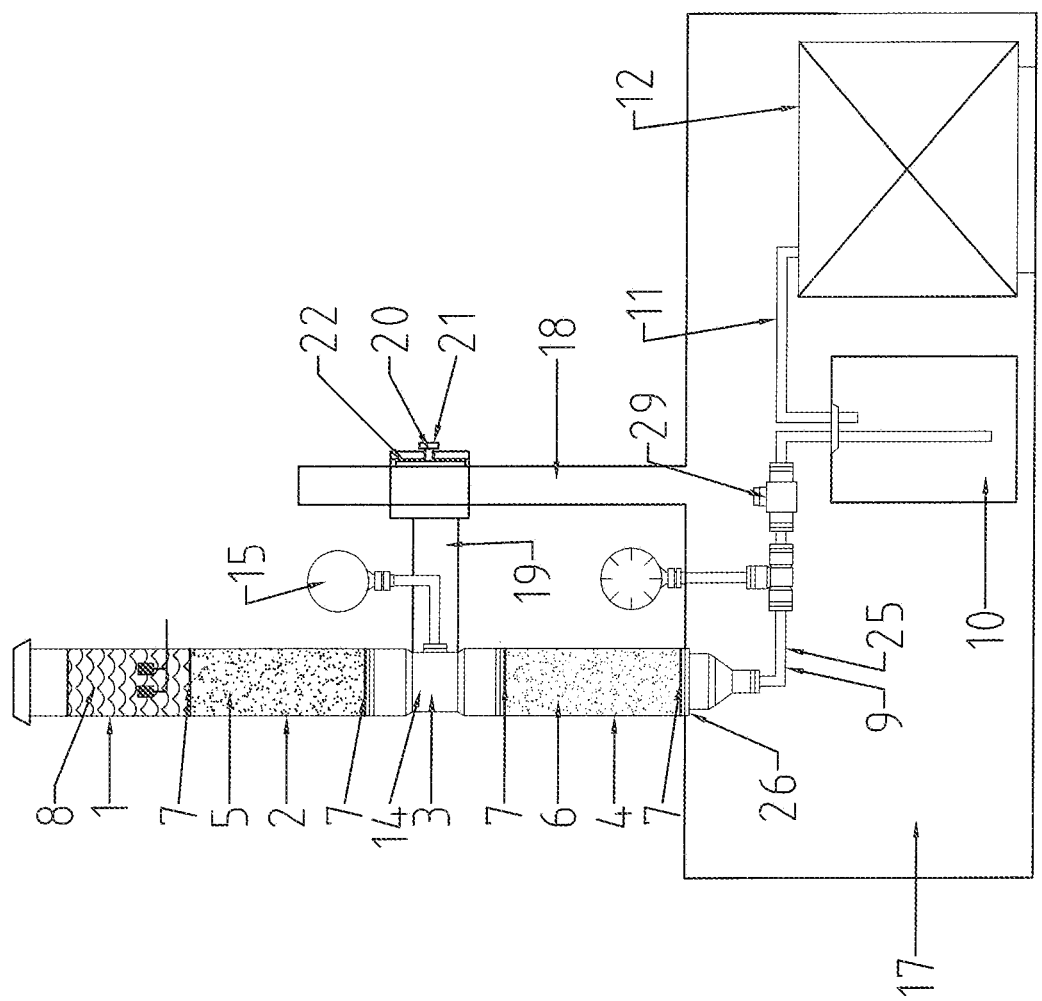
FIG. 5 is a structural representation of the experimental setup for measuring the vacuum degree and pore pressure at a point of soil mass in vacuum consolidated state provided in Embodiment 2 in complete state.
Figure 6:
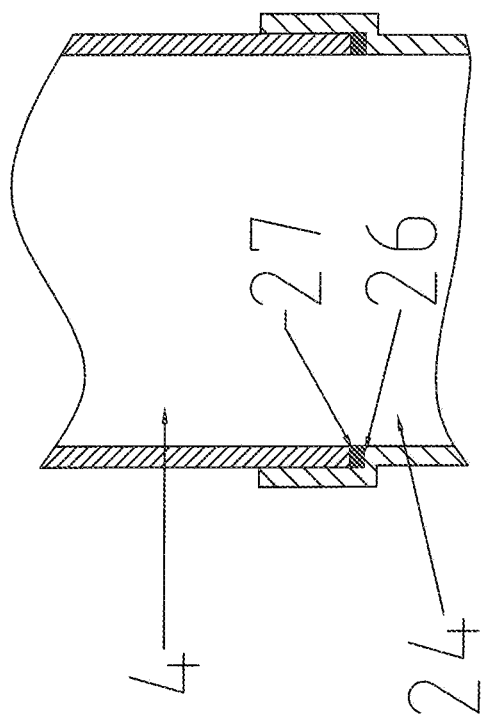
FIG. 6 is a structure section view of upper and lower tubes or port joint in FIG. 5.

As shown in FIG. 3, the upper test soil mass is in a hard tube, the upper end and lower end of the upper test soil mass are covered with a filter membrane 7, the upper test soil mass 5 is sealed with distilled water 8, the distilled water tube is covered with a thin film to guarantee a vacuum environment. The upper filter membrane 7 of the upper test soil mass 5 is connected to a pore pressure gauge 30, the pore pressure gauge 30 is connected to the computer for reading.

As shown in FIGS. 3-6, the test operation method of the experimental setup for measuring the vacuum degree and pore pressure at a point of soil mass in vacuum consolidated state includes the following steps:

A. The middle tube 2 and lower tube 4 are connected in one, and then the middle tube 2 and lower tube 4 are installed on a boring machine, the soil sampling depth is approached by mud drilling, when the soil sampling depth is approached, the descent shall be slow to avoid disturbing the hole bottom soil sample, the middle tube 2 and lower tube 4 are rapidly and continuously pressed in the predetermined depth of soil, and stopped for 3-5 minutes before the soil mass is pulled out:

B. When the middle tube is being separated from the lower tube, the soil mass therein is cut up into an upper test soil mass 5 remaining in the middle tube and a lower experimental soil mass 6 remaining in the lower tube 4, the filter membrane 7 is disposed at the upper and lower ends of the middle tube 2 respectively, the filter membrane 7 is disposed at the upper and lower ends of the lower tube 4 respectively, the lower end of the middle tube 2 is connected to the upper end of the intermediate tube 14, the upper end of the lower tube 4 is connected to the lower end of intermediate tube 14, the lower end of lower tube 4 abuts the abutting port 24, the distilled water 8 is filled in the upper water storage tube 1;

C. After various devices are connected up, the pumping mechanism 12 is actuated, various instruments have readings after a period of time, if the reading of negative pressure vacuum gauge is $k_1$, the reading of negative pressure vacuum gauge is $k_2$, the reading of pore pressure gauge 30 is $k_3$, and the heights of upper experimental soil mass and lower experimental soil mass are fixed at 1, the attenuation law and specific attenuation value are analyzed by comparing the values of $$\frac{k_1 - k_2}{l}$$

and $$\frac{k_2 - k_3}{l}.$$

As shown in FIGS. 1-2, the Embodiment 3 is basically identical with Embodiment 2 of the present invention, the only difference is that the soil particles in the experimental soil mass of Embodiment 3 are replaced by different water contents, porosity ratios and experimental soil mass lengths respectively according to particle size and mass. The check experiment can be performed at the same time (FIG. 2) for experimental contrast and data gathering and analysis.

We claim:

1. An experimental setup for measuring the vacuum degree and pore pressure at a point of soil mass in vacuum consolidated state, including a connecting tube, the connecting tube including an upper water storage tube, a middle tube, an intermediate inner chamber and a lower tube abutting each other, wherein the middle tube is loaded with an upper experimental soil mass, the lower tube is loaded with a lower experimental soil mass, a filter membrane is arranged at the upper and lower ends of the soil masses in the middle tube and lower tube respectively, the filter membrane is pervious, the upper water storage tube stores distilled water, the lower tube is connected to a water storage chamber through an inlet conduit, the water storage chamber is connected to a pumping mechanism through an outlet conduit, a body of the water storage chamber is sealed, the intermediate inner chamber is connected to an upper negative pressure vacuum gauge, the inlet conduit is connected to a lower negative pressure vacuum gauge.

2. The experimental setup defined in claim 1, wherein the upper water storage tube and lower tube are provided with a docking mechanism, the middle tube and lower tube are connected and driven in the soil mass to take the subsurface soil mass.

3. The experimental setup defined in claim 2, wherein an intermediate inner chamber is arranged in an intermediate tube, an upper end of the intermediate tube is connected to the middle tube, and a lower end is connected to the lower tube.

4. The experimental setup defined in claim 3, wherein the connecting tube is provided with a mounting base, the mounting base is provided with a negative pressure vacuum gauge, a water storage chamber and a pumping mechanism, the negative pressure vacuum gauge includes the upper negative pressure vacuum gauge and the lower negative pressure vacuum gauge, the mounting base includes a base, a spindle and a mounting rack, a sleeving hole of mounting rack is fitted over the spindle, moving up and down along the spindle, an unlockable lock bar is arranged at a sleeve joint of mounting rack and spindle, the lock bar is provided with a handwheel, the lock bar is rotationally connected to a locking tile in the sleeving hole through the mounting rack, the intermediate tube is fixed to the mounting rack, the upper negative pressure vacuum gauge is fixed to the mounting rack, the intermediate tube communicates with the upper negative pressure vacuum gauge through an upper channel on the mounting rack; the base is provided with an abutting port for abutting the lower tube, the abutting port is connected to a lower channel on the base, the water storage chamber, the lower negative pressure vacuum gauge and pumping mechanism are fixed to the base, the lower negative pressure vacuum gauge communicates with the lower channel, the outer end of the lower channel is connected to the water storage chamber, the water storage chamber is connected to the pumping mechanism.

5. A test operation method of the experimental setup for measuring the vacuum degree and pore pressure at a point of soil mass in vacuum consolidated state defined in claim 4, including the following steps:

I. the middle tube and lower tube are connected in one, and then the middle tube and lower tube are installed on a boring machine, the soil sampling depth is approached by mud drilling, when the soil sampling depth is approached, the middle tube and lower tube are rapidly and continuously pressed in the predetermined depth of soil, and stopped for 3-5 minutes before the soil mass is pulled out;

II. when the middle tube is being separated from the lower tube, the soil mass therein is cut up into an upper test soil mass remaining in the middle tube and a lower experimental soil mass remaining in the lower tube, the filter membrane is disposed at the upper and lower ends of the middle tube respectively, the filter membrane is disposed at the upper and lower ends of the lower tube respectively, the lower end of the middle tube is connected to the upper end of the intermediate tube, the upper end of the lower tube is connected to the lower end of the intermediate tube, the lower end of the lower tube abuts the abutting port, the upper water storage tube is filled with equilong distilled water;

III. the pumping mechanism is actuated, if the reading of the negative pressure vacuum gauge is $k_1$, the reading of the negative pressure vacuum gauge is $k_2$, the reading of the pore pressure gauge is $k_3$, and the heights of the upper experimental soil mass and lower experimental soil mass, are fixed at l, the attenuation law and specific attenuation value are analyzed by comparing the values of $$\frac{k_1 - k_2}{l}$$

and $$\frac{k_2 - k_3}{l}.$$

6. The experimental setup defined in claim 1, wherein a storage camera aligned with a negative pressure vacuum gauge dial is arranged outside the negative pressure vacuum gauge.

7. The experimental setup defined in claim 1, wherein an electronic readout system is arranged outside the negative pressure vacuum gauge, the electronic readout system is connected to a computer, the computer records the data of the negative pressure vacuum gauge at any time.

8. The experimental setup defined in claim 7, wherein an upper test soil mass is in a hard tube, the upper end and lower end of the upper test soil mass are covered with a filter membrane respectively, the upper test soil mass is sealed with distilled water, a distilled water tube is covered with a thin film to guarantee a vacuum environment.

9. The experimental setup defined in claim 8, wherein an upper filter membrane of the upper test soil mass is connected to a pore pressure gauge, the pore pressure gauge is connected to the computer for reading.

* * * * *